(12) United States Patent
Hunt et al.

(10) Patent No.: US 7,761,410 B2
(45) Date of Patent: Jul. 20, 2010

(54) SYSTEM AND METHOD FOR REVIEWING AND IMPLEMENTING REQUESTED UPDATES TO A PRIMARY DATABASE

(75) Inventors: William A. Hunt, Pittsburgh, PA (US); Jennifer Menicucci, Pittsburgh, PA (US); Howard Minor, Erie, PA (US)

(73) Assignee: Medcom Solutions, Inc., Pittsburgh, PA (US)

( * ) Notice: Subject to any disclaimer, the term of this patent is extended or adjusted under 35 U.S.C. 154(b) by 52 days.

(21) Appl. No.: 11/537,814

(22) Filed: Oct. 2, 2006

(65) Prior Publication Data

US 2007/0088765 A1 Apr. 19, 2007

Related U.S. Application Data

(60) Provisional application No. 60/722,216, filed on Sep. 30, 2005, provisional application No. 60/833,548, filed on Jul. 26, 2006.

(51) Int. Cl.
*G06F 17/30* (2006.01)

(52) U.S. Cl. .................. 707/609; 707/610; 707/674

(58) Field of Classification Search ............. 705/2, 705/4; 707/1–5
See application file for complete search history.

(56) References Cited

U.S. PATENT DOCUMENTS

| | | | | |
|---|---|---|---|---|
| 5,915,241 A * | 6/1999 | Giannini | ................ | 705/2 |
| 5,937,343 A * | 8/1999 | Leung | ................ | 455/403 |
| 6,061,657 A | 5/2000 | Whiting-O'Keefe | | |
| 6,088,677 A * | 7/2000 | Spurgeon | ................ | 705/4 |
| 6,144,941 A | 11/2000 | Hotti et al. | | |
| 6,324,516 B1 | 11/2001 | Shults et al. | | |
| 6,665,647 B1 * | 12/2003 | Haudenschild | ................ | 705/2 |
| 6,810,429 B1 * | 10/2004 | Walsh et al. | ................ | 709/246 |
| 6,873,997 B1 | 3/2005 | Majjasie et al. | | |
| 7,069,227 B1 * | 6/2006 | Lintel et al. | ................ | 705/4 |
| 2001/0041991 A1 * | 11/2001 | Segal et al. | ................ | 705/3 |
| 2002/0069085 A1 | 6/2002 | Engel | | |
| 2002/0120469 A1 | 8/2002 | Javitt | | |
| 2002/0128862 A1 | 9/2002 | Lau | | |
| 2002/0143581 A1 | 10/2002 | Ishii | | |
| 2003/0018496 A1 | 1/2003 | Hambright | | |
| 2003/0074220 A1 * | 4/2003 | Brandt | ................ | 705/2 |
| 2003/0083903 A1 | 5/2003 | Myers | | |
| 2003/0120512 A1 | 6/2003 | Dengler | | |
| 2003/0204420 A1 * | 10/2003 | Wilkes et al. | ................ | 705/3 |
| 2004/0024749 A1 | 2/2004 | Kusens | | |
| 2004/0128165 A1 | 7/2004 | Block | | |
| 2004/0199406 A1 | 10/2004 | Owens | | |
| 2004/0220865 A1 | 11/2004 | Lozowski | | |

(Continued)

*Primary Examiner*—Mohammad Ali
*Assistant Examiner*—Huawen Peng
(74) *Attorney, Agent, or Firm*—Alicia M. Passerin, Esq.; Cohen & Grigsby, P.C.

(57) ABSTRACT

The invention is a system that reviews, approves, and implements updates to a primary database that houses a business's chargeable items. A duplicate database has a duplicate of each data entry in the primary database. Prior to implementation, the update is reviewed for compliance with regulatory and local standards and preapproved updates by using the duplicate database as a point of reference. The management service may revise the update before implementing the update into the primary database. Preferably any update that is implemented into the primary database is validated to confirm that the implemented update matches the approved update.

40 Claims, 21 Drawing Sheets

U.S. PATENT DOCUMENTS

| | | | |
|---|---|---|---|
| 2004/0243433 A1* | 12/2004 | Akin et al. ................... | 705/2 |
| 2004/0267572 A1 | 12/2004 | Emery | |
| 2005/0033604 A1 | 2/2005 | Hogan | |
| 2005/0033609 A1 | 2/2005 | Yang | |
| 2005/0102158 A1 | 5/2005 | Maeda | |
| 2005/0137910 A1 | 6/2005 | Rao et al. | |
| 2006/0173811 A1* | 8/2006 | Gustin et al. ................... | 707/2 |

* cited by examiner

See CM Process Documentation

| TrackingID | ClientCode | Facility | CurrentStatus | ChangeType | Date | Name | SIMDepartment | FIMDepartment |
|---|---|---|---|---|---|---|---|---|
| 6752 | | MedCom | At Finance | C | 3/9/2006 | | CRE | 416 |
| 6753 | | MedCom | At Finance | C | 3/9/2006 | | CRE | 416 |
| 6756 | | MedCom | At Finance | A | 3/9/2006 | | CRE | 416 |
| 8324 | | MedCom | At Consultant | A | 5/11/2006 | | SPD | 376 |
| 8337 | | MedCom | At Consultant | A | 5/12/2006 | | DCD | 383 |
| 8338 | | MedCom | At Consultant | A | 5/12/2006 | | SUH | 661 |

SYSTEM AND METHOD FOR REVIEWING AND IMPLEMENTING REQUESTED UPDATES TO A PRIMARY DATABASE

CLAIM OF PRIORITY

This application claims priority to U.S. Provisional Application No. 60/722,216, filed on Sep. 30, 2005, and U.S. Provisional Application No. 60/833,548, filed on Jul. 26, 2006.

COPYRIGHT NOTICE

This disclosure is protected under United States and International Copyright Laws. © 2005 MedCom Solutions, Inc. All Rights Reserved. The copyright may be assigned by MedCom Solutions, Inc. to another individual or other entity without advance notice. While the copyright owner has no objection to the reproduction of the patent document as it appears in the Patent and Trademark Office patent files and records for informational purposes, the copyright owner reserves all other rights and remedies under the United States copyright laws which pertain to this disclosure.

FIELD OF THE INVENTION

The present invention relates generally to a system that implements requested updates to a primary database, and more specifically to a system that uses a duplicate database as a point of reference to review the requested update prior to implementing the update in the primary database. The system may optionally include a management service, such as an internal supervisor or an external consulting service that also reviews the requested update. The present invention also relates to a method of electronically implementing requested updates to a database.

BACKGROUND

Computerized methods for reviewing a business's database that houses or has the business's chargeable supplies or services are known in the art. For example, in the health care industry, hospitals and physicians use databases called item masters, chargeable item masters, or chargeable item databases to house descriptions of all of the chargeable supplies and services that they provide. In order for a hospital to be able to collect on billed claims, its item master must be compliant with federal regulations because claims are generated based on the information contained in the item master, including pricing, codes, and descriptions of chargeable items. Thus, errors in the item master can affect a hospital's or a physician's ability to collect on a claim. Additionally, computerized methods for periodically reviewing these databases for compliance are known in the art. However, given the frequent changes in federal and local regulations governing the health care industry, it is increasingly difficult for those in charge of billing for these institutions to keep up with these changes and to ensure that the information contained in the database is compliant and accurate with applicable regulations and standards. Incorrect entries in the database can have serious consequences. For example, a given hospital may lose millions of dollars in annual reimbursements when patients are either undercharged or not charged at all for goods or services received. Additionally, inconsistent entries between departments in a given institution mean that one department may be undercharging for a given service, thus cutting into the institution's overall reimbursements. In some instances, noncompliant entries in the item master can even lead to claims arising under the False Claims Act.

It is an arduous task for hospital administrators to implement the frequent changes in health care billing regulations and when changes are implemented, it is difficult for administrators to confirm that the changes have been entered correctly.

SUMMARY OF THE INVENTION

Thus, there is a need for a system that accurately implements changes to a business's database. The present invention meets this need by providing a system that implements an update to a primary database that houses or has data entries such as line items for a business's chargeable items. There is a duplicate database that is a duplicate of the primary database and that houses a duplicate of each data entry housed in the primary database. Prior to implementing the requested update into the primary database, the update is reviewed electronically or by the management service for compliance with pre-approved updates to the data entry by referring to the duplicate database as a point of reference. If the update is non-compliant the update may be revised. A report that summarizes approved updates to the primary database is generated and the update is implemented. Preferably, any update that is implemented into the primary database is validated after entry to confirm that the implemented update matches the approved update.

In another embodiment, the present invention is a method of implementing a requested update to a database.

It is an object of the present invention to provide a system that reviews and implements a requested update to a business's database.

It is a further object of the present invention to provide a system that uses a duplicate of the primary database to provide a point of reference for reviewing a requested update to the primary database.

It is also an object of the present invention to provide a system that reviews and implements a requested update to a hospital's or physician's item master.

It is a further object of the present invention to provide a system that reviews a requested update for compliance with pre-approved updates or regulatory or entity standards.

It is yet a further object of the present invention to provide a system that assigns a unique tracking identification number to each requested update to the primary database.

It is still a further object of the present invention to provide a system that stores and date and time stamps a history of each requested update to the primary database for historical and auditing purposes.

It is a further object to provide a method for maintaining consistency between chargeable items within the primary database of multiple entities or departments.

It is a further object of the present invention to provide a method of implementing at least one update to the database.

It is a further object of the present invention to provide a method of monitoring the status of requested updates to a primary database.

Other objects, features, aspects and advantages of the present invention will become better understood or apparent from the following detailed description, figures, and appended claims of the invention.

BRIEF DESCRIPTION OF THE DRAWINGS

FIGS. 3 to 22 show an example of a series of screenshots that are displayed to and used by a user of the claimed system.

DETAILED DESCRIPTION OF EMBODIMENTS OF THE INVENTION

Figure 1:
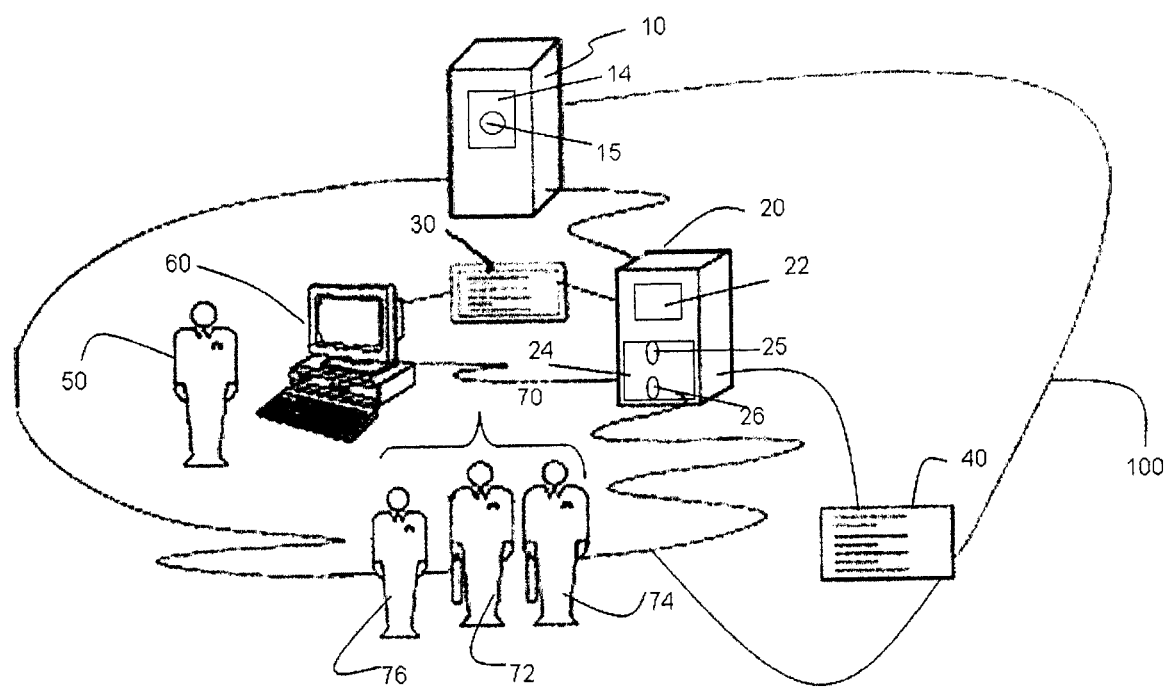
FIG. 1 shows a schematic of an example of an embodiment of the claimed system.

In an example of an embodiment, the present invention is directed to a system 100 that reviews and implements an update to a primary database 15. Following approval, updates to the primary database 15 may be implemented immediately or they may be marked for implementation at a specific time and date in the future. The primary database 15 houses a plurality of data entries and is preferably stored on a computer-readable storage medium 14. In an example, the data entries housed in the primary database 15 are either technical or professional chargeable items, or both. For example, the chargeable items may include billable items, non-billable items, and/or statistical items. For each chargeable item in the primary database 15 there is at least one field or line item. In an example, the primary database 15 is a hospital's or physician's item master or chargeable item master or chargeable item database that houses data entries related to all of the chargeable supplies and services that the entity provides. In the example where the business is a health care entity, technical chargeable items may be hospital charges for services and supplies and professional chargeable items may be physician surgical services.

Line items may include, for examples, a code to identify the chargeable item, the name of the facility providing the supply or service (i.e., the chargeable item), a short or long description of the supply or service, a designation indicating which department(s) within the business provide the supply or service, and/or a price that is charged for providing the supply or service. Each business may optionally have its own internal coding system that is comprised of a plurality of unique identifiers that designate each of the chargeable items housed in the primary database 15. For example, a business may use service codes (i.e., alpha or numeric codes) that are assigned to identify chargeable items. In another example, a business may use internally created procedure codes to designate or identify chargeable items. Alternatively, the code or the price charged for the good or service may be derived from one of a plurality of entities that publish standards to regulate the business. For example, where the business is a healthcare business such as a hospital, the American Medical Association (AMA) publishes Current Procedural Terminology (CPT®) codes that are used to designate procedures or services provided by a physician.[1,2] Similarly, Medicare publishes HCFA Common Procedure Coding System (HCPCS) codes that may be used to designate particular supplies or services provided by a healthcare business. In yet another example, a private entity or business may develop its own unique codes to designate particular goods or services. As other examples, many private insurance carriers and HMOs each publish fee schedules of what that entity will pay for a given supply or service.

[1] CPT® is a trademark of the American Medical Association.
[2] Current Procedural Terminology (CPT) is a copyright 2005 American Medical Association. All Rights Reserved. No fee schedules, basic units, relative values, or related listings are included in CPT. The AMA assumes no liability for the data contained herein. Applicable FARS/DFARS restrictions apply to government use.

The primary database 15 is capable of being updated. Updates may be any edit or change to the data entries housed in the primary database. In an example, the update is an addition of a data entry such as an addition of a chargeable item or at least one field or line item of a chargeable item. In another example, the update is a removal or deletion of data entry such as the removal of a chargeable item or at least open field or line item of a chargeable item. In yet another example, the update is an activation, inactivation, or reactivation of at least one of the fields of a chargeable item housed in the primary database. In an example where the primary database 15 houses chargeable items for a hospital or physician's practice, the update may be to at least one of the following fields: CPT code, description, modifier, revenue code, price, or statistic, where a statistic includes items for which the hospital or practice cannot charge.

FIG. 1 shows an example of an embodiment of the system 100 that comprises at least one processor 22 that uses at least one set of instructions 26 to implement at least one update to the primary database 15. The system further comprises a duplicate database 25 that is a duplicate of the primary database and that houses a duplicate of each data entry in the primary database 15. The duplicate database 25 is used so that updates are not implemented into the primary or original database 15 in realtime until the requested update 30 is approved. The duplicate database 25 has a corresponding data entry for each data entry in the primary database. Instructions 26 and the duplicate database 25 are stored on a first storage medium 24. Preferably, the processor 22 and first storage medium 24 are components of a second unit 20, such as for example a computing unit. The primary database 15 is stored on a second storage medium 14. Preferably, the second storage medium 14 is a component of a first unit 10, such as for example a computing unit. First and second storage media 14, 24 may be computer readable. A processor 22 (described below) uses instructions 26 to duplicate the primary database 15 and to store the duplicate database 25 on the first storage medium 24. There is an authorized user 50 who requests at least one update 30 to the primary database 15. The processor 22 uses instructions 26 to convert the requested update 30 and the corresponding data entry to a readable format. The instructions 26 also direct the processor 22 to generate a report 40 that summarizes an approved update to the primary database 15. The approved update is implemented into the primary database 15. Optionally, disapproved requested updates may be included in the report, but disapproved updates are not implemented into the primary database 15.

In an example, the system 100 is embodied in a computer system. The components contained in the computer system are those typically found in general purpose computer systems, and in fact, these components are intended to represent a broad category of such computer components that are well known in the art.

An authorized user 50 requests the update 30 to the primary database 15. Preferably, each authorized user 50 has an authorized user identification code or password that identifies the user as being authorized to access and/or request updates to the primary database 15. In an example, the authorized user 50 is an administrator who works for or is employed by the business. The authorized user 50 may be in charge of maintaining and updating the database. In another example, the authorized user 50 is a member of the management service 70. The management service 70 may be internal to the business or entity, such as an administrator 76, or may be an external consulting service comprised of regulatory 72 and/or financial 74 consultants. Preferably, and as shown in FIG. 1, the authorized user 50 submits the request 30 electronically, such as by an input device 60 that preferably comprises a portal, described in detail below. In other examples, however, the request 30 may be submitted verbally or as a paper submission and may optionally be submitted directly to the management service 70 (not shown).

The requested update 30 may be either a single update to one data entry or a plurality of updates to more than one data entry. Only requested updates submitted by an authorized user 50 will be converted to a readable format by the processor 22, where readable formats include those that are computer-readable, readable by one of the consultants 72, 74, the administrator 76, or a combination thereof. In an example, a parser program imports the requested update 30 into the processor 22 and the processor 22 uses the instructions 26 to convert the requested updates 30 into a readable format. The parser program may also import the corresponding data entry (i.e., a data entry in the duplicate database that corresponds to the data entry in the primary database 15 for which the update was requested) from the duplicate database 25 into the processor 22. Then, the processor 22 uses the instructions 26 to convert the corresponding data entry to a readable format.

Referring again to FIG. 1, the system 100 also comprises a first storage medium 24 that stores in part, at least one set of computer-coded instructions 26, described below, the duplicate database 25, and a processor 22. If the system 100 is implemented in software, the storage medium 24 stores the executable code when in operation. The main memory may include banks of dynamic random access memory as well as high-speed capable memory. Where the system 100 is a computer system, the processor 22 may contain a single microprocessor, or may contain a plurality of microprocessors for configuring the computer as a multi-processor system. The processor 22 uses the instructions 26 to process the requested update 30, as described below. The components contained in the computer systems 10, 20 are those typically found in general purpose computer systems, and in fact, these components are intended to represent a broad category of such computer components that are well known in the art.

Preferably, the set of instructions 26 comprises at least one set of instructions that are used by the processor(s) 22 to duplicate the primary database 15. Preferably, the primary database 15 is duplicated at regular time intervals, such as daily or weekly. Each time the primary database is duplicated, the duplicate database 25 is archived on the first storage medium and replaces or overwrites the preceding duplicate database for use as the reference point as described above.

Figure 10:
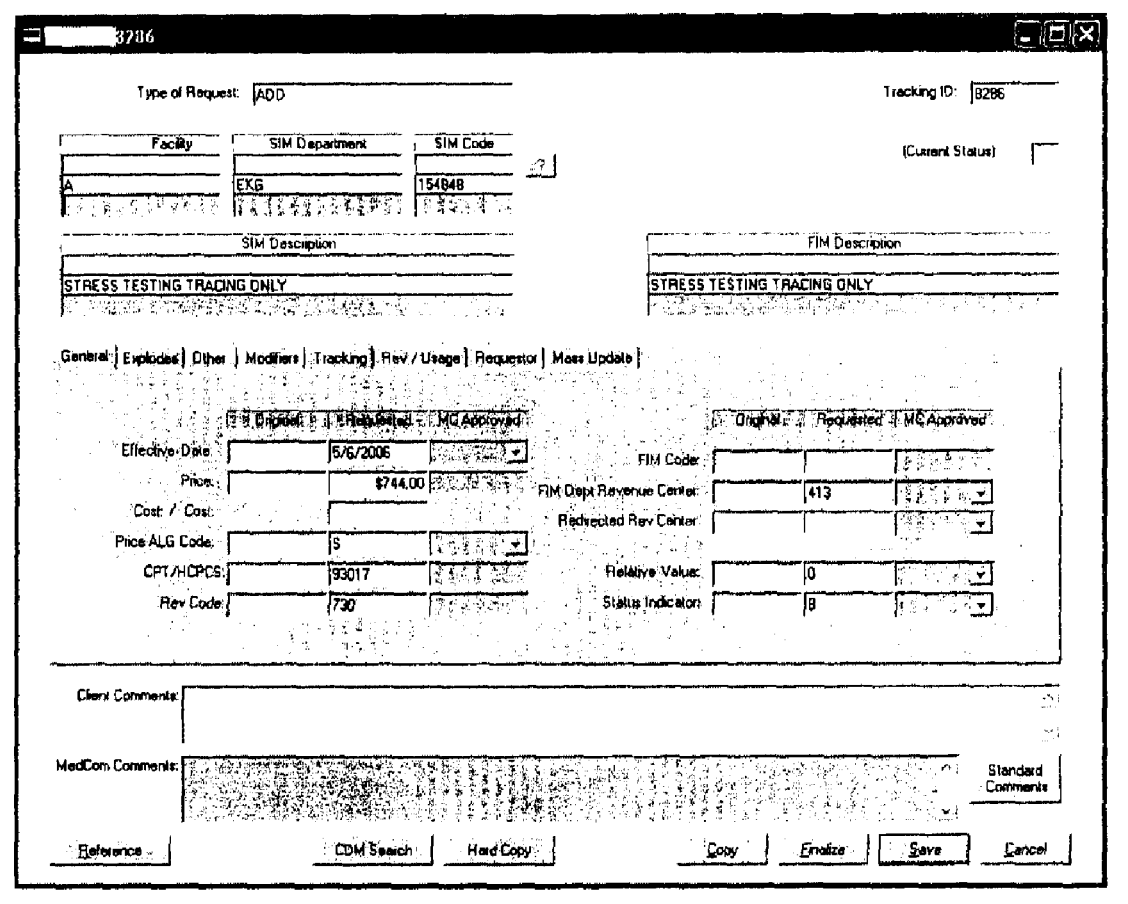

The processor(s) 22 uses at least one set of instructions 26 to convert the requested update 30 to a readable format. In a preferred example, the readable format displays a tracking ID, the type of requested update (i.e., addition, reactivation, inactivation, change, etc.), and the actual fields that the authorized user is requesting be changed (for example, price, codes, description, accounting fields, system flags, etc.). The readable format may include the original line item as it appears in the primary database 15 and the requested update so that the consultant can compare the original data entry and the requested change 30. In a more preferred example, there is also a field into which the consultant may enter an approved update. The approved update may be the same as the requested update or may be a revised or corrected update. An example of this readable format is shown in FIG. 10.

The processor(s) 22 uses at least one set of instructions 26 to convert the corresponding data entry in the duplicate database 25 to a readable format, as described above.

The processor 22 uses at least one set of instructions 26 to generate a report 40 that summarizes approved updates 30 to the primary database 15. The report 40 details, field by field, the data that need to be uploaded into the database in order to implement an update to the primary database 15. The update is approved after the request 30 is reviewed by the management service 70, the processor 22, or both. There may be a set of instructions 26 that approve updates to be uploaded into or mapped onto the primary database 15, or the approved updates may be manually entered by the management service 70. Optionally, there is also at least one set of instructions 26 that directs the processor(s) 22 to review the requested update 30. The review may include confirmation or determination of compliance with at least one pre-approved update to the data entry. Preapproved updates are those that conform to applicable entity standards, and those that maintain or implement consistency between departments within the business or optimal pricing standards. Entity standards may also be derived from industry codes and regulations, fee schedules, or structural limitations built into the primary database such as limitations on the number of characters allowed in the description of the item. Preferably, the review of a requested update includes a review of all of the fields of a chargeable item, including CPT or HCPCS codes, description, revenue code, modifier(s), price, accounting codes, and any applicable system flags. In an example, system flags are toggle buttons that indicate whether or not a supply or service can be billed as having a volume of more than one. Additionally, entity standards may include unique codes, descriptions, or fee schedules created by the business for internal use with the primary database.

As part of the review, the processor 22 may use the instructions 26 to revise or correct the request when the request does not comply with preapproved updates to the data entry comprising the primary database 15. Examples of requested updates to which the processor 22 could make amendments include price, relative value unit, and revenue code. In the example of price, the processor 22 uses the instructions 26 to revise the requested update 30 where price in the primary database 15 is less than a given fee schedule amount. In the example of relative value unit (RVU) (which is a scaling system used to define how much work and non-work by a physician goes into a procedure), the processor 22 uses the instructions 26 to revise the requested update 30 if the work and/or non-work scale values are less than a given number. In the example of revenue code, which are Medicare-derived codes, the processor 22 uses the instructions 26 to revise the requested update 30 if the code is incorrect for the general service category of the chargeable item.

Optionally, as part of the review, the processor 22 may also use the instructions 26 to flag or identify the request 30 when the request does not comply with at least one preapproved update. For example, where the business is a hospital and where the CPT code entered for the requested update does not comply with the CPT code for that service, the program may flag the requested update 30. The processor 22 may use the instructions 26 to substitute a preapproved update, or the consultant may manually revise the request 30 and substitute an update.

In order to display textual and graphical information, the system 100 contains the graphics subsystem and the output display (not shown). In an example, the readable formats are displayed on an output display. The output display may include a cathode ray tube display or a liquid crystal display. The graphics subsystem receives textual and graphical information and processes the converted requested update and corresponding data entry from the duplicate database for display on the output display. A graphical user interface (GUI) designed to collect certain information regarding data entries or chargeable items can be used to facilitate entry of the requested update and the corresponding data entry.

The system may further include a mass storage device, peripheral devices, portable storage medium drives, input control devices, a graphics subsystem, and an output display (not shown). The computer system may be connected through one or more data transport means. For example, the processor and the main memory may be connected via a local microprocessor bus, and the mass storage device, peripheral devices, portable storage medium drives, and graphics subsystem may be connected via one or more input/output (I/O) busses. The mass storage device, which may be implemented with a magnetic disk drive or an optical disk drive, is non-volatile storage device for storing data and instructions for use by the processor. In the software embodiment, the mass storage device stores the information software for loading to the main memory.

In an example, the system 100 further comprises a management service 70. The management service 70 that is capable of reviewing, evaluating, amending and/or approving the requested update 30 prior to generating the report 40. In an example, approval to implement the requested update 30 is granted when the request is compliant with all entity and other standards or requirements or has been amended to be compliant. In an example the management service 70 comprises either an internal administrator 76, an external consulting service that is comprised of at least one regulatory consultant 72 and at least one financial consultant 74, or a combination thereof. The internal administrator 76 can perform any function or review that is carried out by the external consulting service, and particularly the regulatory and financial consultants 72, 74. Preferably every review by a regulatory consultant 72 includes a review of at least regulatory coding, price, accounting codes, and information system flags. In an example, the processor 22 may use the instructions 26 to review these also. The regulatory review ensures, for example, coding accuracy or compliance with entity standards, correct format for the business's item master, and/or consistency across all departments of the business. For example, where the business is a hospital or other healthcare business, the regulatory consultant 72 may review the requested update for coding compliance with the AMA published CPT codes or Medicare HCPCS codes that are used to designate particular services and/or supplies provided by a healthcare provider. The regulatory consultant may also confirm that the short and/or long description of the service or supply being described in the primary database complies with the data structure of the primary database. For example, the primary database 15 may limit the number of characters that a given description may have. Additionally, applicable entity standards may place limitations or impose restrictions on the descriptions of a given supply or service. Finally, the regulatory consultant 72 may review and compare the requested update 30 to make sure that the same service or supply is described or coded consistently between departments of the same business where more than one department offers the same supply or service.

The regulatory consultant 72 is also capable of correcting, revising, or changing the requested update 30. Where, for example, the regulatory consultant's 72 review or evaluation determines that the requested update 30 is inconsistent or non-compliant with entity standards or pre-approved updates, the regulatory consultant 72 may revise the requested update to be consistent or compliant. Furthermore, in an embodiment, the regulatory consultant 72 may revise requests identified or flagged by the processor as being non-compliant or inappropriate. In an embodiment, during the review, the consultant 72 may refer to the reference materials such as those that may be included in the portal, described below. Examples of regulatory reference materials include websites for Medicare and Medicaid that provide CPT and other codes and descriptions, fee schedule amounts, RVU tables and modifier tables.

The financial consultant 74 is capable of reviewing the requested update to ensure assignment of an appropriate code for the chargeable item, appropriate data structure for accounting, and consistency of pricing across departments of the same business where more than one department offers the same good or service. The financial review may also include review to ensure compliance with applicable entity standards or financial compliance. For example, where the business is a hospital or other healthcare business, and where the requested update 30 is a fee change, the financial consultant 74 may review the requested update for compliance with the fee schedules of entities such as Medicare, private insurers, and HMOs. Preferably, the requested update 30 to a fee is at least equal to, and more preferably is greater than, the fee schedules of the entities described above in order to maximize the business's reimbursements. The financial consultant 74 is also capable of amending the requested update 30 and/or approving the requested update 30 as described above for the regulatory consultant 72.

Optionally, the system further comprises an input device by which the authorized user inputs the requested update. In an example, the input device 60 has an input control device and an input display. The input control device(s) provide a portion of the user interface for a user of the computer system. The input control devices may include an alpha numeric keypad for inputting alphanumeric and other key information, or a cursor control device, such as a mouse, a trackball, a stylus, or cursor direction keys. In order to display textual and graphical information, the computer system contains the graphics subsystem and the input display. The input display may include a cathode ray tube display or a liquid crystal display. The graphics subsystem receives textual and graphical information and processes the submitted input for display on the input display. A graphical user interface (GUI) designed to collect certain information regarding chargeable items can be used to facilitate entry of input.

In an example, the input device 60 comprises a portal. In an embodiment, the portal is encoded in software. In another example, the portal is a web-based application. The authorized user 50 is able to submit input, including an authorized user identification and the requested update. Optionally, the portal has a search function that permits an authorized user to search the duplicate database. The search allows searching on any of the line items in the duplicate database. The results of the search may be displayed in a format that may be exported to a software-based file such as Excel. In an example, the portal pulls in all of the data fields for a given chargeable item related to the requested update. The requested update may be submitted for review, as described above.

The portal may also provide a link to a plurality of tools, such as for example, reference tools or tables and links to websites such as regulatory websites. The portal may also enable an authorized user to monitor the status of a requested update. The portal may also be a means of internal review by providing an authorized user access to review its own database (preferably the duplicate database) to identify chargeable items for which updates should be requested because they are out of date, do not comply with entity standards, or do not maximize reimbursements. Finally, the portal may allow or enable the authorized user 50 to review the requested update 30.

In another example, the system 100 may further comprise a means for validating the implemented update to the database to confirm that the implemented update matches the approved update in the report. Preferably, the processor(s) 22 uses a set of instructions 26 to run an algorithm, for example, to compare the approved update to the implemented update. In another example, the validation is performed by the consulting service 70, such as by manually comparing each actual entry with each approved entry.

In another example, the system 100 may further comprise a means for storing and date stamping every requested update 30 to the primary database 15.

Figure 2A:
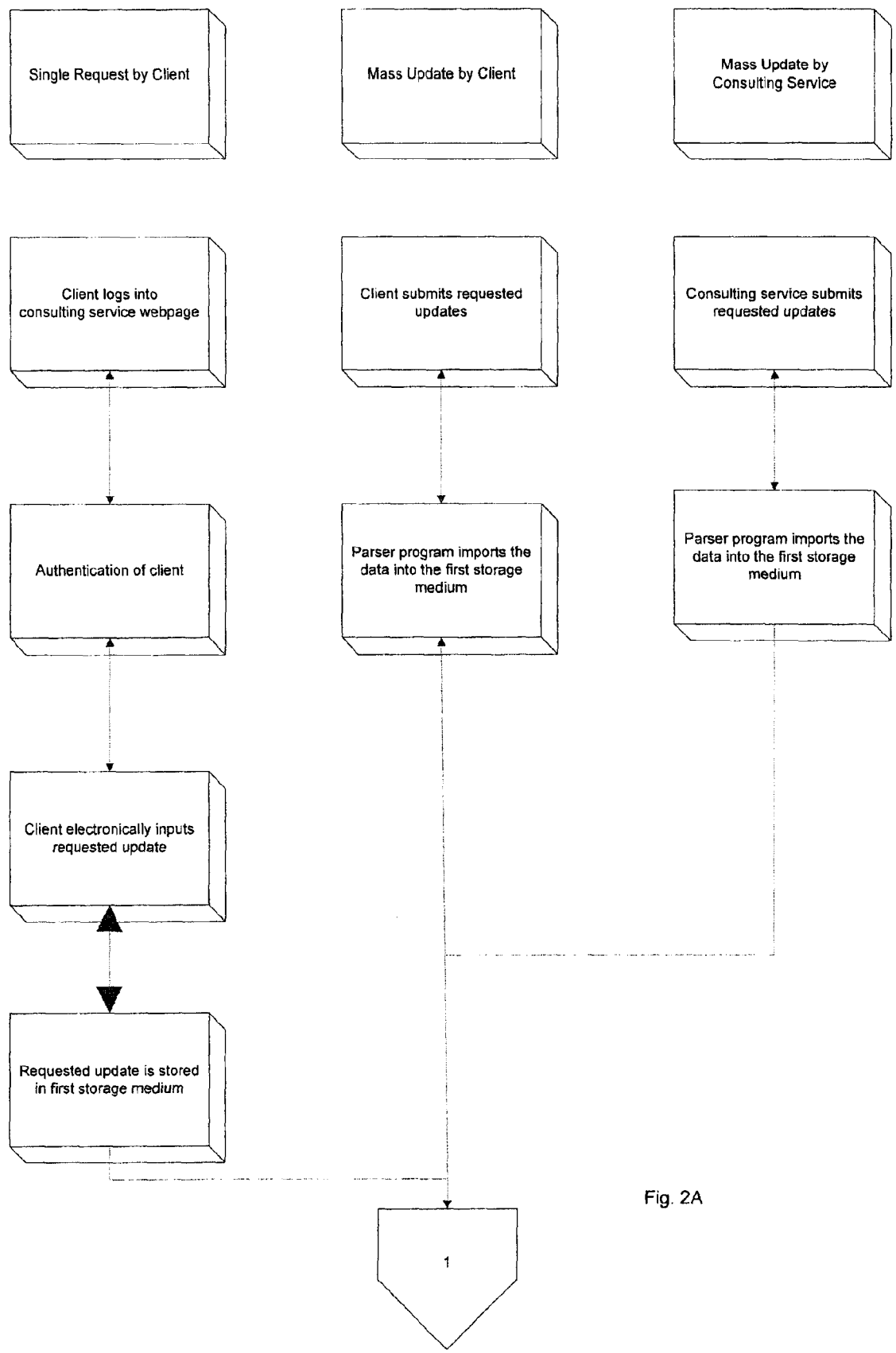
FIGS. 2A-2D show flow diagrams of an example of an embodiment of the claimed method.
Figure 2B:
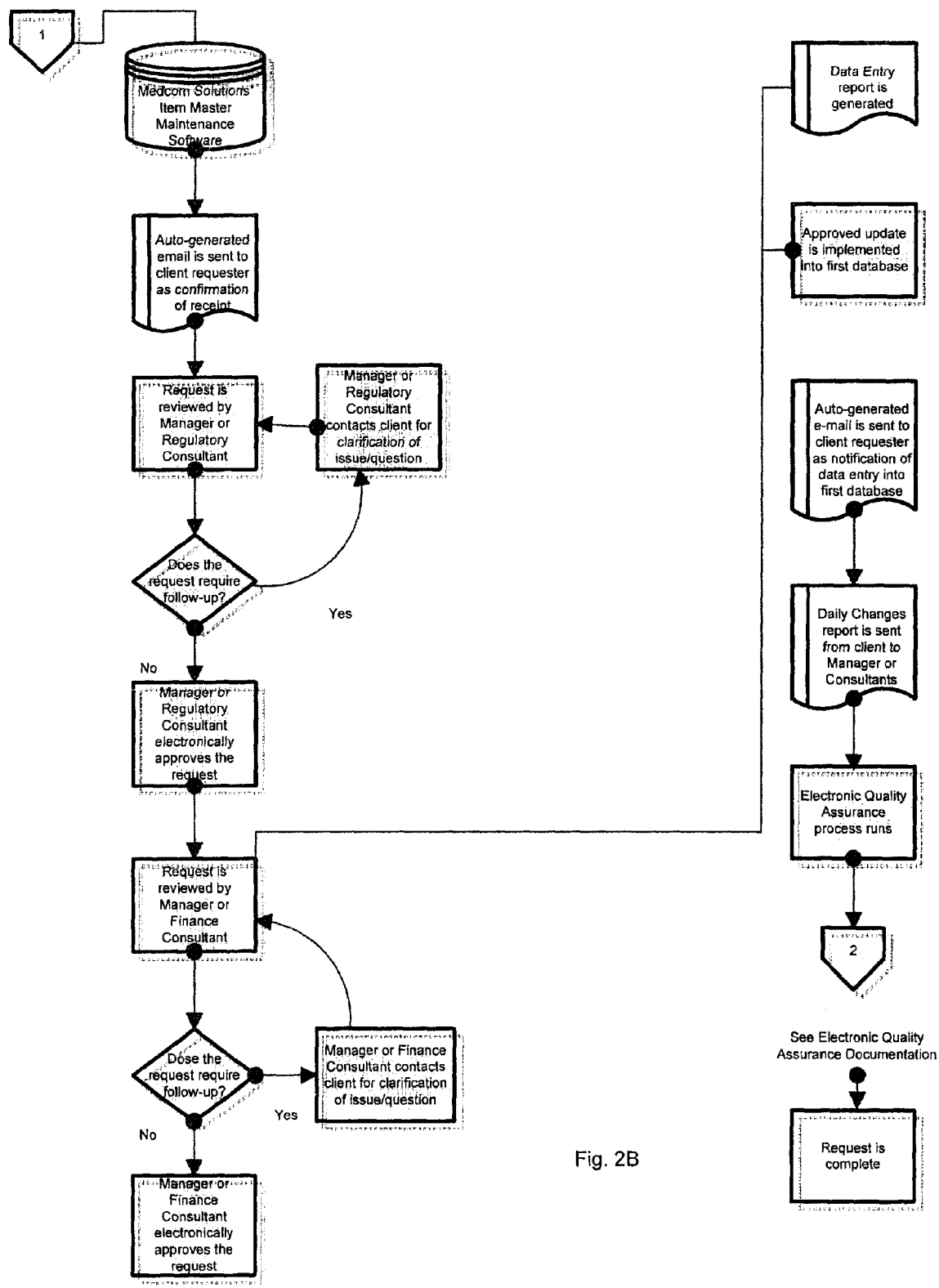
Figure 2C:
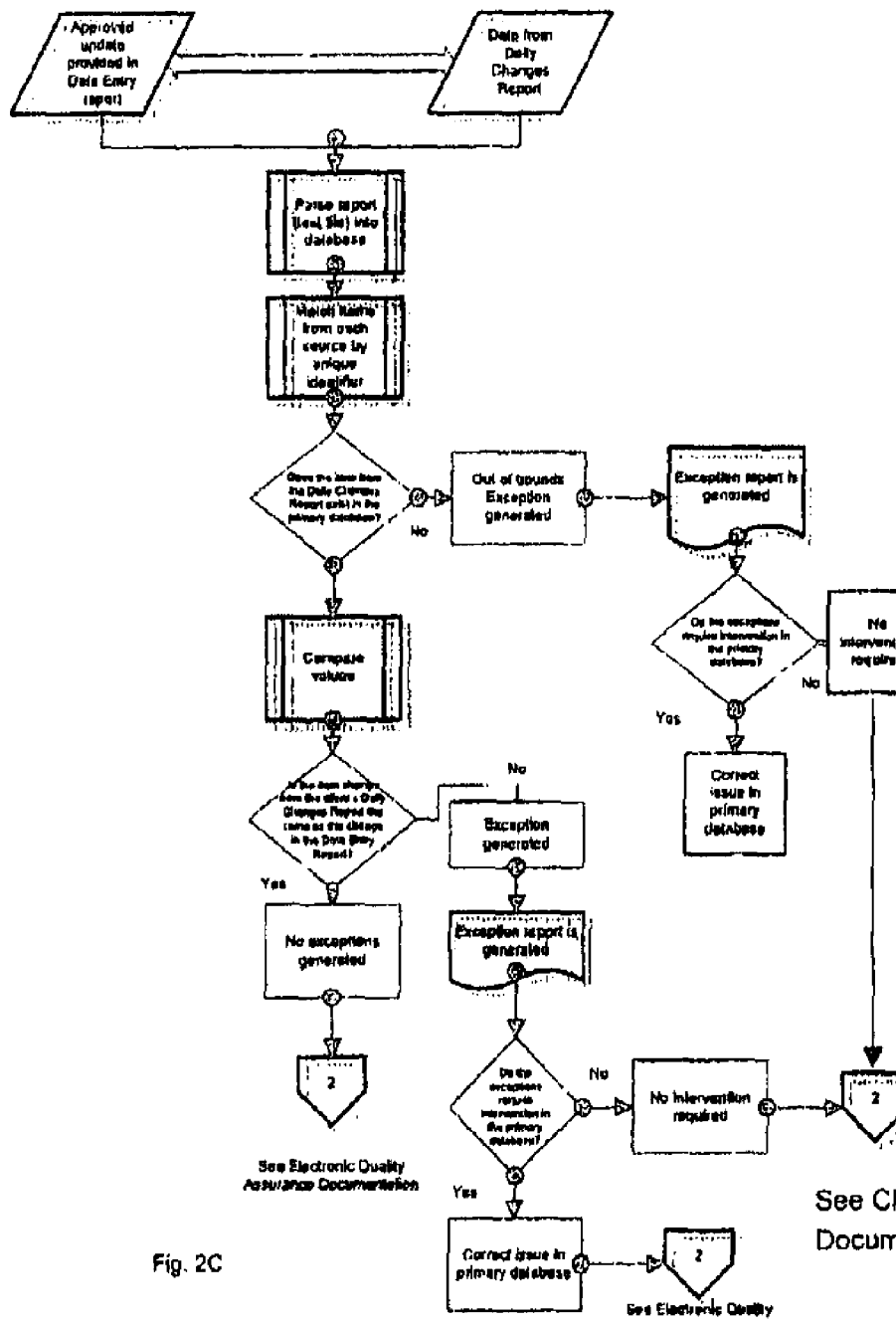
Figure 2:
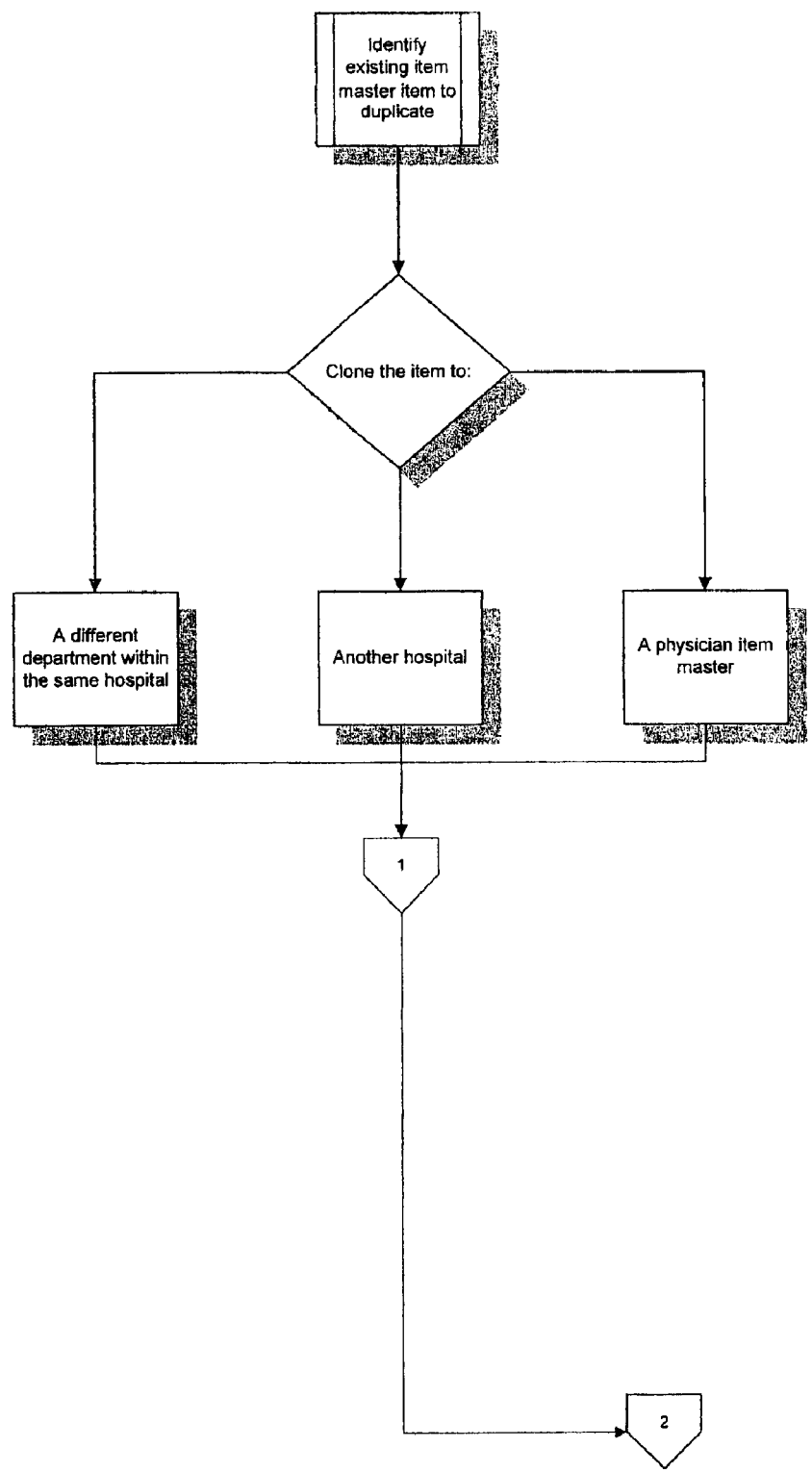

In another embodiment, a method of using the claimed system 100 to review and implement at least one requested update 30 to the first database 15 is described. FIGS. 2A-2C are flow diagrams that show an example of a preferred embodiment of the method of using the system 100 to review and implement requested updates. The method shown is only intended to be an example and is not meant to be limiting in any way. The method can be performed without requiring all of the steps shown. As shown in FIG. 2A, the first step of the claimed method is for an authorized user to request an update to the primary database 15. In a preferred example, the request is submitted via the portal, described above. The authorized user 50 may be a client, such as a business, hospital, or physician's practice. In another example, the authorized user 50 may be the consulting service 70. As described in more detail above, the requested update may be, for examples, an addition of at least one data entry, a change to at least one data entry, or removal of at least new data entry. Preferably, the step of requesting the update includes entering or providing an authorized user identification code or password.

FIG. 2A also shows that in an example, the requested update 30 is a single request. In this embodiment, an authorized user 50 logs into, for example, the portal using an authorized user identification or password. After authentication of the authorized user's identification code, the authorized user 50 submits the requested update 30 using, for example, forms provided in the portal. The request 30 is then converted to a readable format by the processor 22 for subsequent review. In another example, the requested update 30 is a mass update comprised of a plurality of requested updates to the primary database 15. The mass update may be requested by either an authorized user 50 or by the management service 70. Requested mass updates may be submitted using the portal or they may be submitted directly to the management service 70. In a preferred example, a parser program imports the mass updates to the processor 22 for review and possible implementation. In an example, mass updates are performed as part of a proactive review of a business's primary database to confirm that, for example, the primary database conforms to entity, regulatory, or financial coding or pricing requirements, that data entries are consistent between multiple departments within the same business, that the business is maximizing its revenue, or that certain services need to be added or inactivated as chargeable.

In another example shown in FIG. 2D, an approved updated item is identified for cloning in another primary database 15, such as when the same chargeable item appears in primary databases of different departments within the business or hospital, another related business or hospital, or within a physician's item master. Cloning is important because it is a method for maintaining consistency between chargeable items within the primary database 15 of multiple entities or departments.

As shown in FIG. 2B, the requested updates 30 are converted to a computer readable format by the processor 22 as described above. Optionally, the method may comprise the step of sending an email to the authorized user 50 who submitted the requested update to confirm receipt of the submission. Next, the processor 22 uses the instructions 26 to review the requested update 30 as described above (not shown). Preferably the management service 70 also reviews the requested update 30. In a more preferred example, a regulatory and a financial consultant each review the requested update. Optionally, the authorized user 50 who requested the update 30 may be contacted by the processor 22, management service 70, or both for clarification of the requested update. Contact may be electronic, such as an email that is sent to the authorized user 50, or may be personal, such as a telephone call that is placed to the authorized user 50. The contact may be automatically generated by the software such as by email, or may be initiated by the consulting service such as by email or by a telephone call from the management service 70 regulatory and/or financial consultant. Where the request does not comply with preauthorized updates, the step of reviewing the requested update may include revising or changing the requested update 30 to make the requested update 30 compliant (not shown). In a preferred example, the review by each consultant 72, 74 or administrator 76 includes at least a review of the following fields or line items: regulatory coding, pricing, accounting codes or general ledgers, and information system flags that are automatically activated by the software when a requested update is noncompliant or erroneous. Preferably, where the requested update 30 is to a field or chargeable item in the technical database, the field or item in the professional database is automatically reviewed for compliance and/or consistency.

Next, the requested update 30 is approved by the software, processor or regulatory and/or financial consultant. Preferably, the approval is performed by both the processor 22 and the management service 70. In the example shown in FIG. 2B, the regulatory consultant 72 reviews and approves the requested update prior to the financial consultant's 74 review and approval.

Following approval of the requested update, a report is generated that details at least the approved update. This report is labeled "Data Entry" report in FIG. 2B. Preferably, the processor 22 uses the computer-coded instructions 26 to generate the report 40.

The approved update may be electronically entered into the primary database 15 or it may be entered manually. In the example shown in FIG. 2B, the approved update is entered via a secure electronic connection. Data entry may be made manually by a consultant 72, 74 or administrator 76 who enters the approved update into the primary database 15 or the update may be mapped into or uploaded into the primary database 15. In the example shown in FIG. 2B, the authorized user 50 who requested the update is sent an email notification that the primary database 15 has been updated.

In an optional step, a changes report (not shown), generated at regular time intervals and preferably daily, is sent by the business to the management service 70 that itemizes updates or changes made to the primary database 15 during the most recent time interval. In an example, the changes report is used for validation of the implemented update, described below.

In a preferred example, the method further comprises the step of validating the implemented update to the primary database 15 to confirm that the update that was actually implemented into the primary database 15 matches the approved update provided in the report 40. In an example, the validation is an electronic quality assurance that preferably uses an algorithm. In an example, the changes report is parsed by a parser program into a table that is stored within a report database (not shown) that is housed in the first storage medium 24 in and is used to compare the changes that were requested and approved. The steps comprising the validation are detailed in FIG. 2C. As shown, the updates listed in the Data Entry report 40 are compared to the updates listed in the changes report. In an example, the algorithm determines if the update in Data Entry report appears or was implemented in the primary database. If it does, then the approved update is compared to the daily changes report. Where the update in the approved update report matches the update (shown by the Daily Changes Report), no exception is granted, the update is unchanged, and the update is validated and the method of reviewing and implementing a requested update is concluded. Where the update in the approved update report is different from the implemented update, an exception report is generated. The consulting service determines whether or not the exception requires intervention in the primary database. In an example, an immaterial error, for example, where there is a spacing error, does not require intervention and the update is validated. In an example where the error is material, such as a coding error, the incorrect entry is corrected in the primary database, and then the update is validated. In an example where a change was made to the primary database 15 that was not implemented by the inventive system 100, an out of bounds exception will occur. The system 100 identifies such an exception by comparing the approved updates with implemented changes itemized on the changes report. An out of bounds exception is any change made to the primary database 15 that was not an approved change. These changes may originate from changes made directly to the primary database by such person who has direct access to the primary database 15.

Optionally, the method may further comprise the step of the authorized user 50 monitoring the status of the requested update 30. In a preferred example, the authorized user 50 monitors the status by accessing the portal, which provides information to the authorized user 50 as to the status of the request 30, such as for example if the request has been approved, implemented, or validated.

EXAMPLE

FIGS. 3-22 show an example of a series of screen shots that are displayed to and used by an authorized user when a requested update is made and reviewed or implemented in the primary database. Specifically, this series of screen shots are intended to serve as an example of how a requested update to a hospital's item master (i.e., primary database) can be submitted using the claimed system and method. This series is provided for instructional purposes only and is in no way intended to limit the scope of the invention. In this particular example, an authorized user wants to update the hospital's item master to add a "stress testing tracing," labeled in FIG. 10 as "Stress Testing Tracing Only" as a chargeable item in the item master using the portal.

Figure 3:
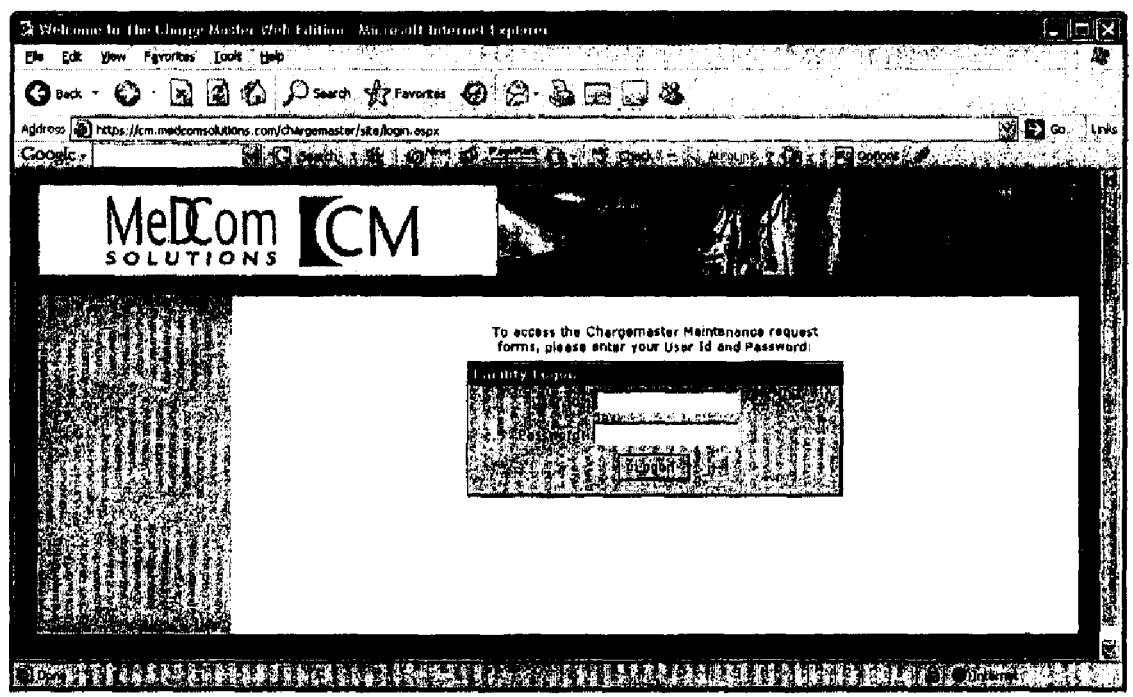
Figure 4:
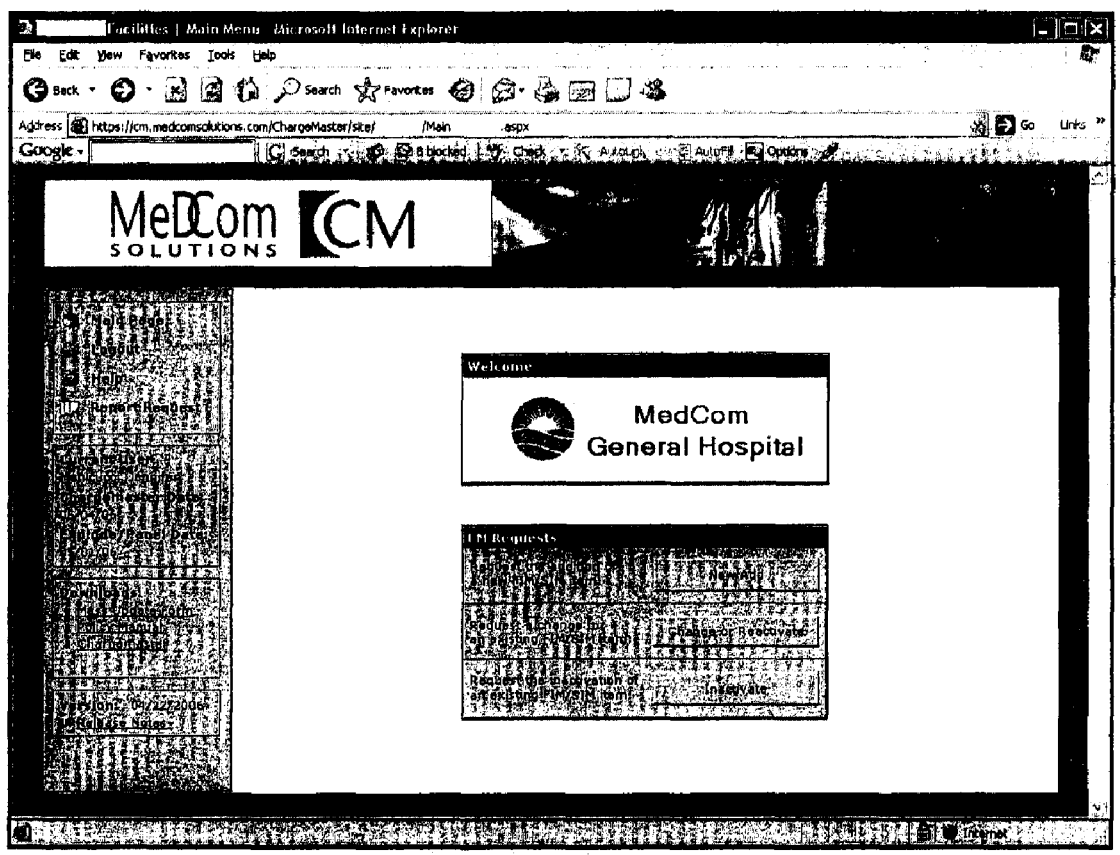
Figure 5:
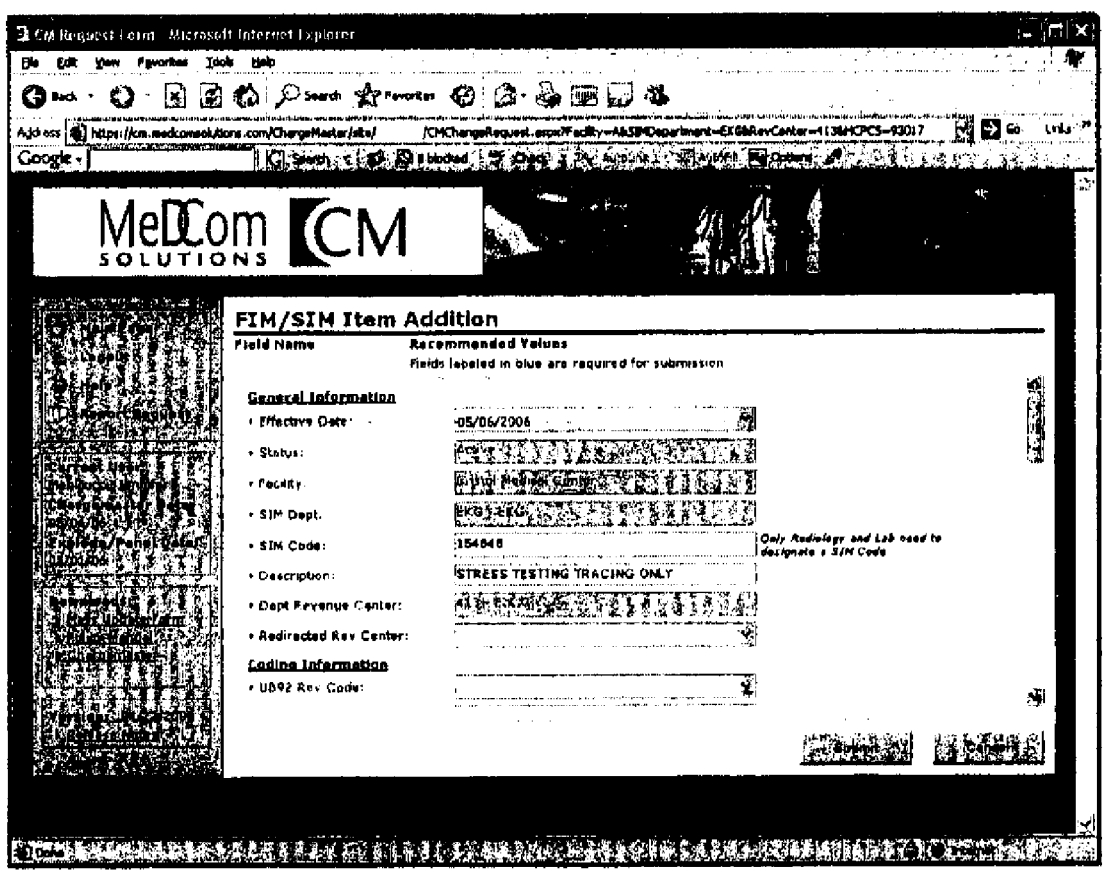

As shown in FIG. 3, the portal has a log-in screen for gaining access to the request forms. This limits access to the system to authorized users. After the user enters the user ID and password, the user is directed to the portal's main page, shown in FIG. 4. The main page of the portal allows the user to navigate through the portal to access the portal's modules. In the example shown, the authorized user has the option of adding to, changing, or reactivating, or inactivating an item in the item master. The user clicks the appropriate choice to continue the update. In this example, the user would click on "New Add" because the update is the addition of a chargeable item, the "stress testing tracing."

After the user selects the type of update, a form is loaded that prompts the user to enter key information related to the update. The form may provide existing data or line items for the chargeable item, such as facility, coding, pricing information, and professional information. In the example shown in FIG. 5, the user is prompted to enter information because this is an "Item Addition." Preferably, the user should submit all of the information they know about the item to be added, including a description of the service and any relevant billing and pricing codes. Optionally, the user may include comments to help explain the reason for the requested update. The completed form is submitted to the consulting service for processing when the user clicks "Submit."

Figure 6:
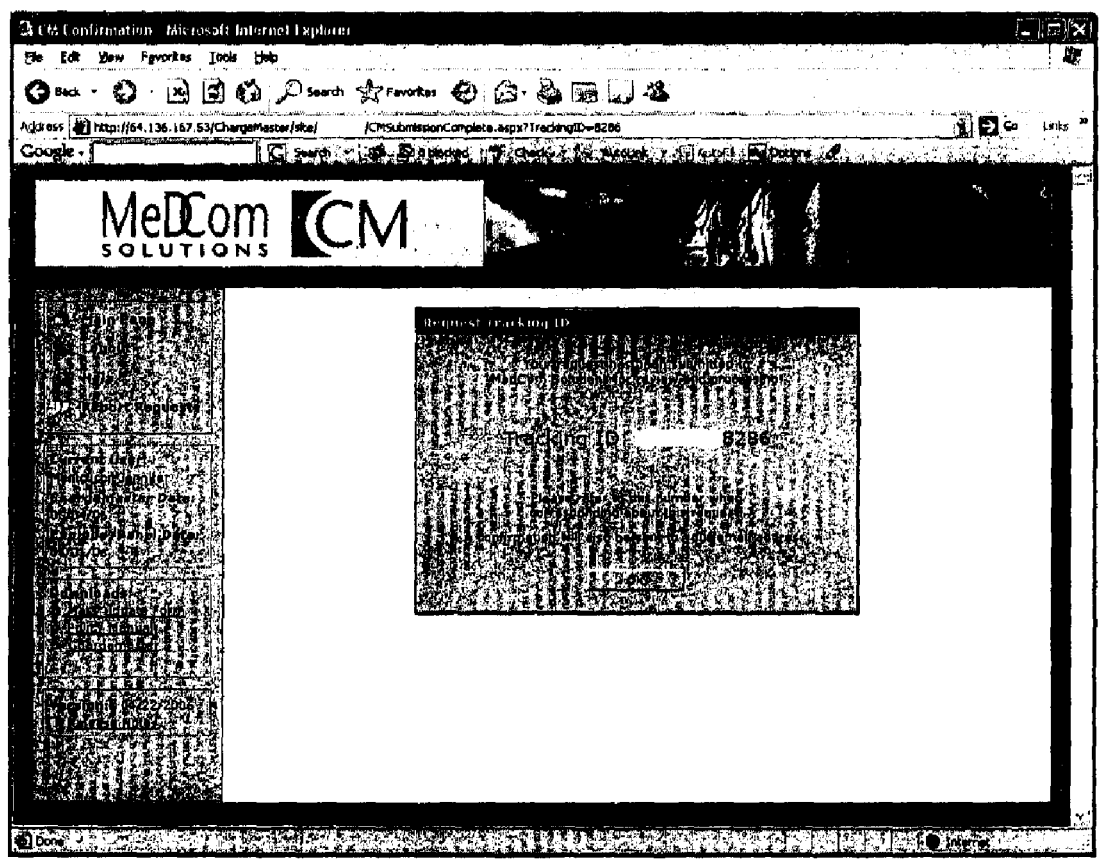
Figure 7:
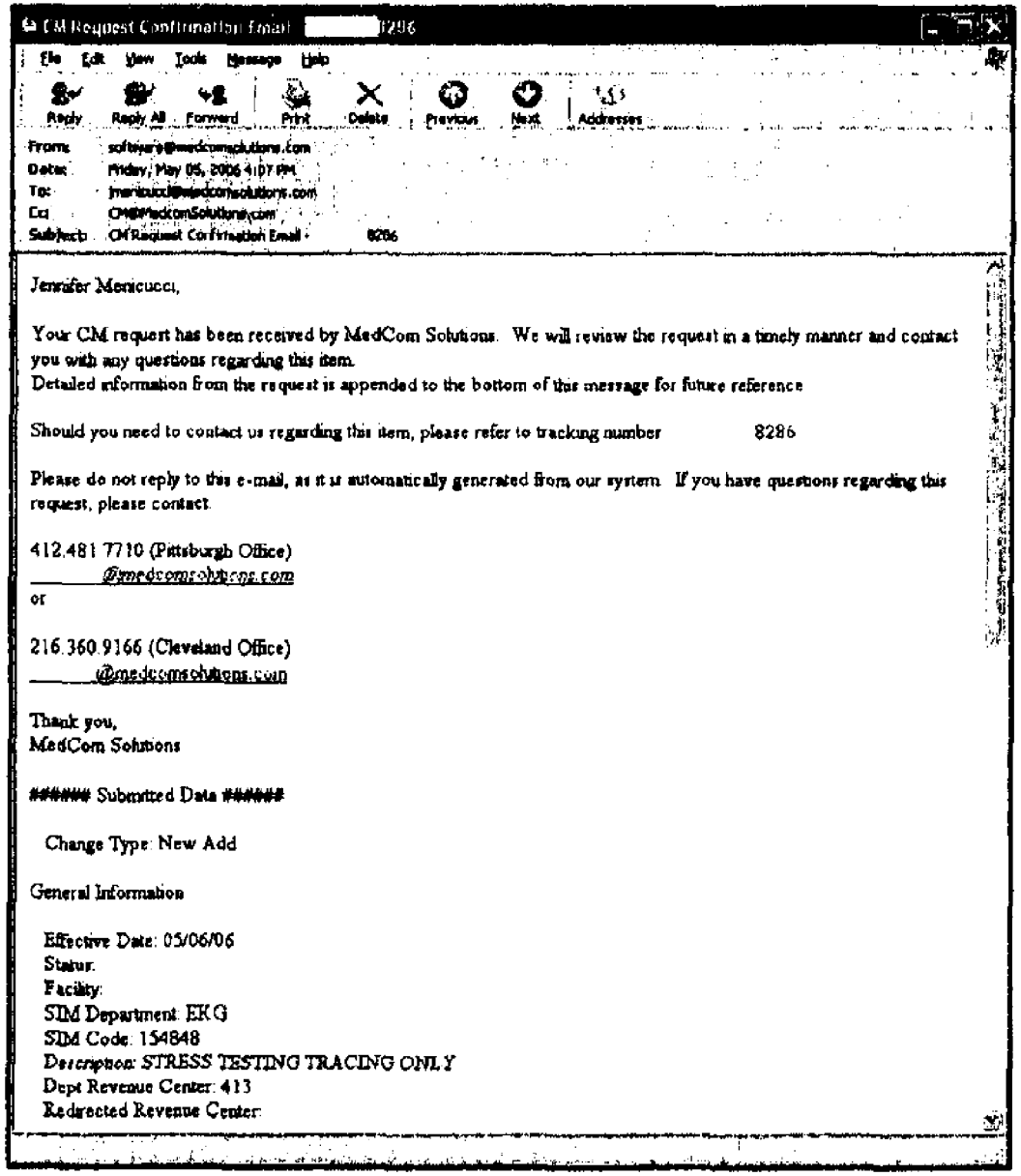

As shown in FIG. 6, the user is provided with a tracking number that refers specifically to the requested update. Also, the user may optionally receive a confirmation email such as the one shown in FIG. 7 that the consulting service has received the requested update. As shown, the email may include the tracking number, a summary of the type of update requested, general information related to the request, and contact information by which the user can contact the consulting service directly.

Figures 8, 9:
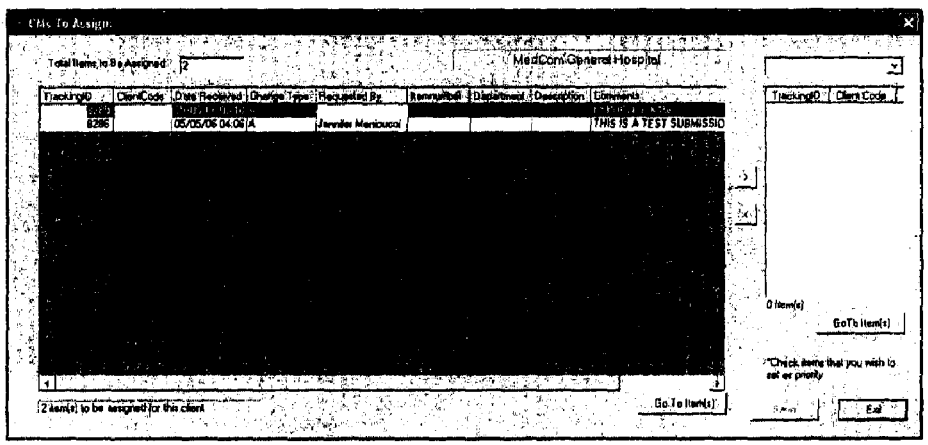

A screen shot showing the assignment form is shown in FIG. 8. An administrator at the consulting service logs into a secure site to access requested updates. The administrator then assigns each request to a consultant and preferably to a regulatory and financial consultant. Preferably, assignments are made based on area of specialty. The administrator is able to place the requested update into the assigned consultant's queue from the screen shown. The administrator has the option to designate a request a priority.

Consultants check their inboxes regularly to review the requests assigned to them. An example of a screen shot of a consultant's inbox is shown in FIG. 9. The consultant selects a request to open and review the request.

An example of the screen shot for consultant review is shown in FIG. 10. The regulatory consultant reviews the request to ensure that it accurately reflects the service or good being provided and is compliant with regulatory guidelines. For example, the regulatory consultant confirms that the descriptions, billing codes, and system flags are compliant with regulatory policies from Medicare, any other payors and facility-specific guidelines established by the hospital or health system.

As shown in FIG. 10, the consultant is presented with specific information about the requested update, including "Original," which shows the data entry as it currently appears in the primary database, "Requested," which shows the requested update submitted by the user, and "Approved," which shows the approved following review by the processor, consultant(s), or a combination thereof, and any necessary changes or revisions to the requested update. The "Original" column will be populated for all types of updates except adds. In the current example, the requested update is an "Addition" and therefore the "Original" column is blank.

In this example, the requested update is to add a "Stress Testing Tracing Only" as a chargeable item. The "Effective Date," "Price," and various "Code" fields are populated with requests as shown in FIG. 10.

Figure 11:
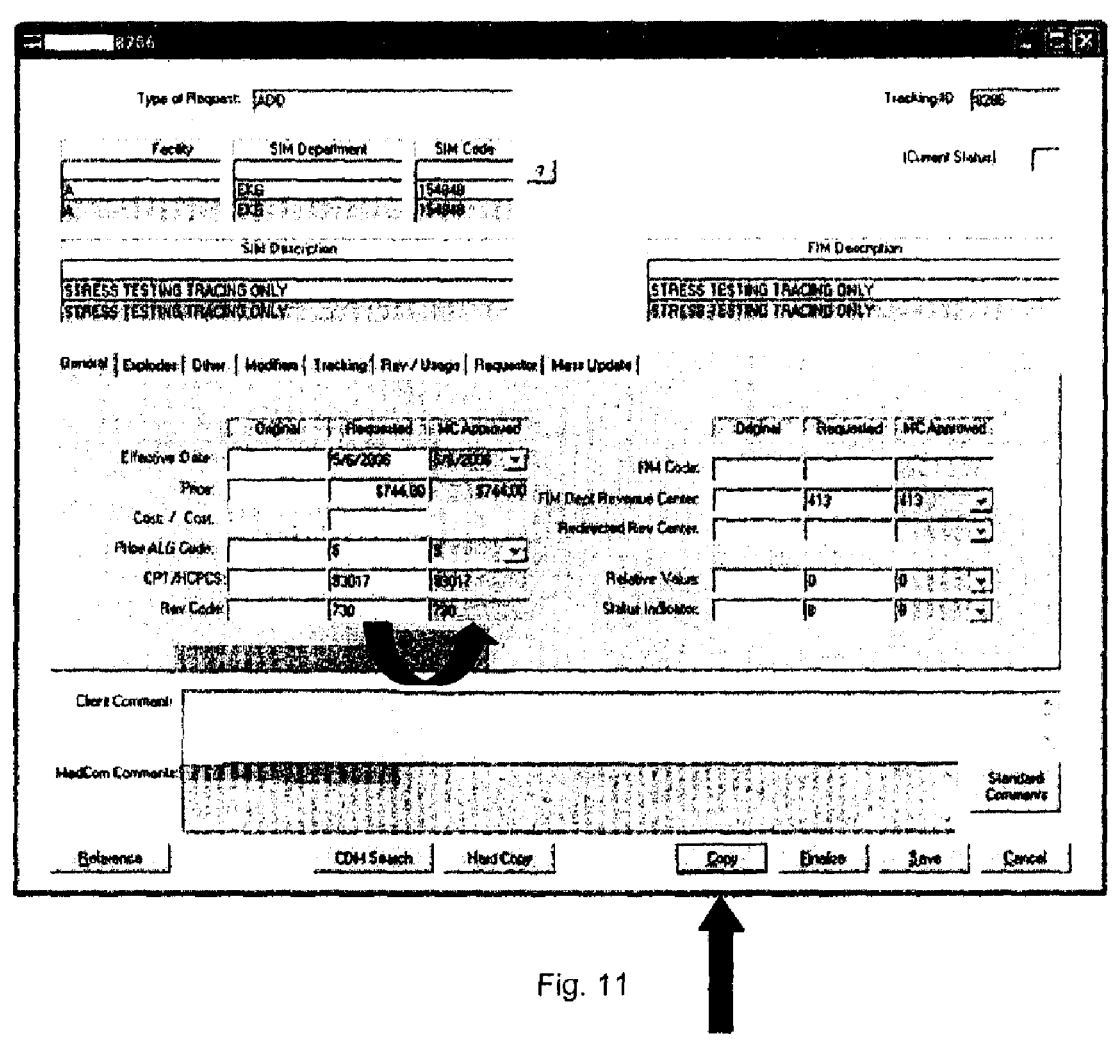

The "Approved" column is shown populated in FIG. 11. Here, the requested update is approved as submitted, so the data in the "Requested" column are copied into the "Approved" column by clicking the "Copy" button.

Figure 12:
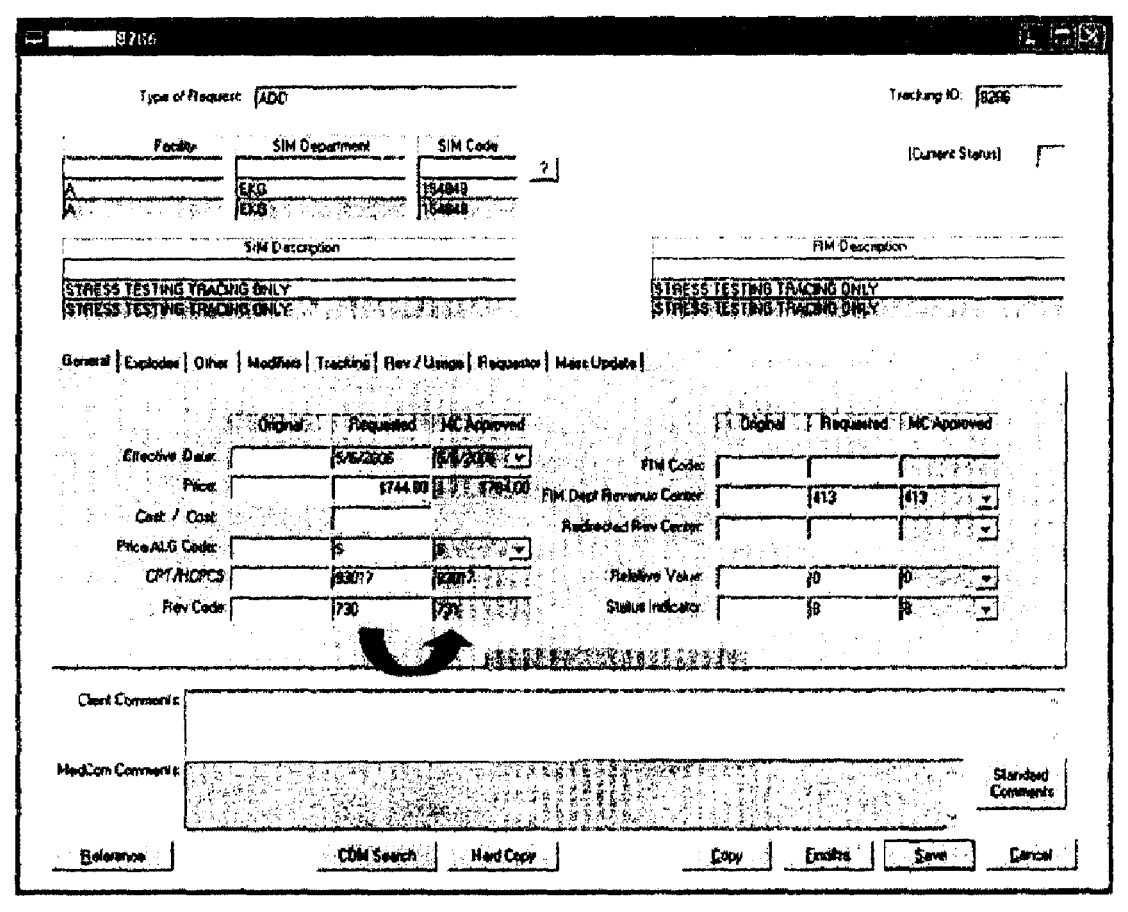

FIG. 12 shows an example of a screen shot in which the requested update is revised by the consultant. In the example shown, the Revenue Code ("Rev. Code") was incorrectly entered as "730" in the request. As shown, the consultant revised the Rev. Code to be "731." The consultant can optionally contact the authorized user to clarify any outstanding issues or questions. When all questions have been resolved and the request is approved, either as originally requested or as revised, the consultant clicks the "Finalize" button. The software stores the finalized request and the date and time that the request was finalized. The request is then sent to the financial consultant's queue.

The financial consultant reviews the request to ensure that it complies with financial guidelines. The screen used by the financial consultant and the steps necessary to review and finalize the requested update are the same as those used by the regulatory consultant shown in FIGS. 11 and 12.

Figure 13:
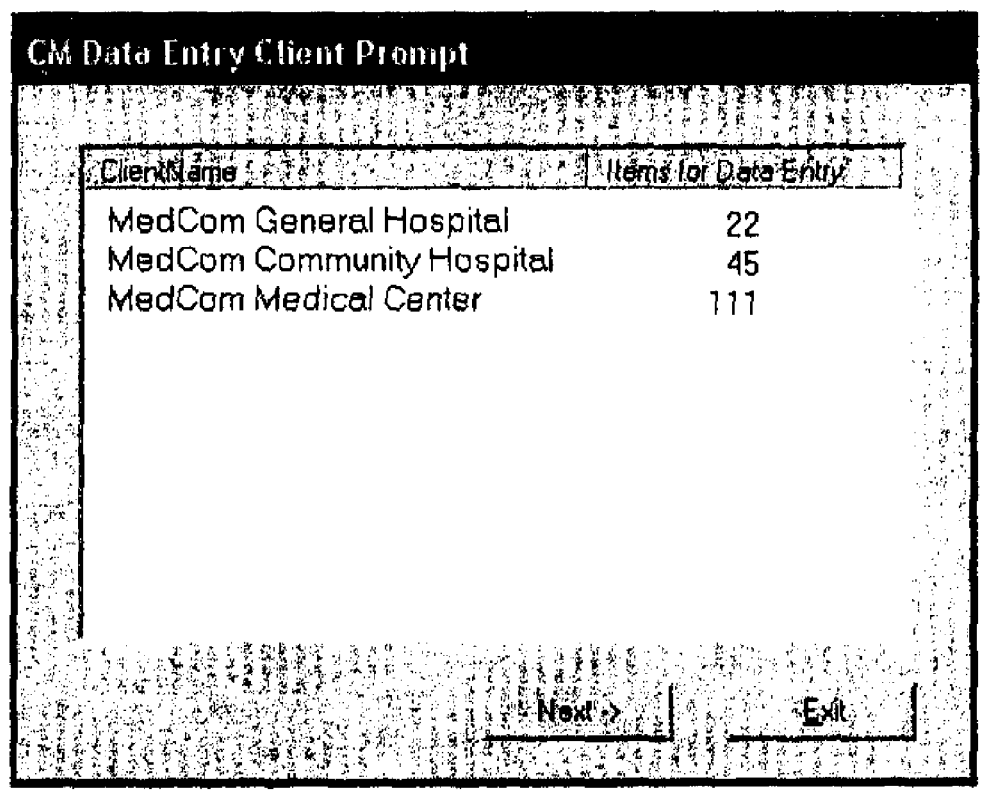
Figures 14, 15:
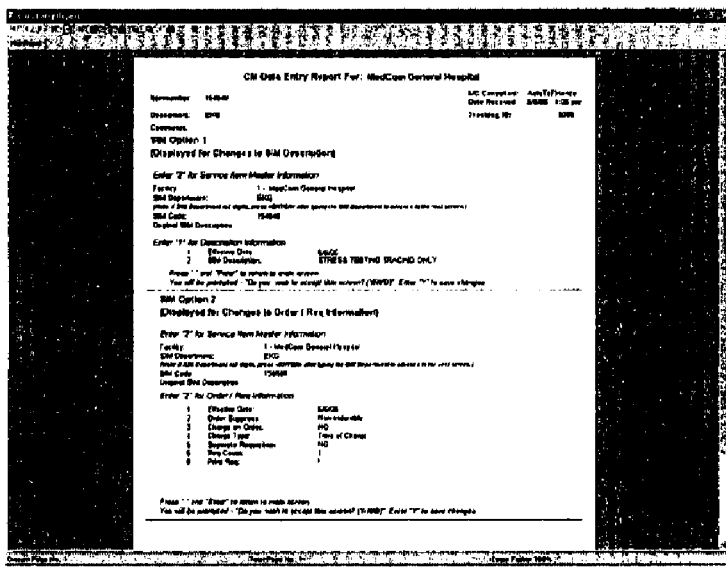

After the requested update is approved, a data entry prompt is sent to notify the consulting service that the request has been approved and a data entry report can be generated, as shown in FIG. 13. An example of the print/preview window for the Data Entry report is shown in FIG. 14. In this example, the data entry report is used by a consultant to manually enter the approved updates into the item master. As shown in FIG. 15, the consultant checks off entered updates.

Figures 16, 17:
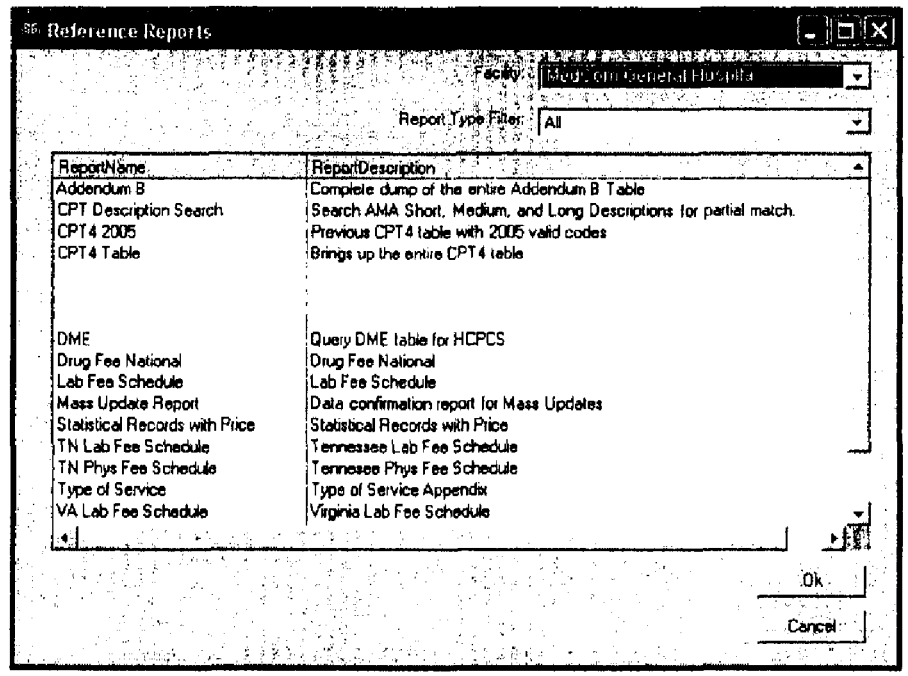

At any time during the review, the consultant can access reference tools or links to websites through the portal. These resources may be used to assist the consultant in his review, revision, and/or approval of the requested update. Preferably, the resources available are customized to a particular client to optimize the resources available to a given business, based on that business's industry or particular needs and because regulations may vary from location to location and depending on the industry in which the business is engaged. FIG. 16 shows an example of resources or utilities that are available to a hospital. When the consultant selects a specific utility from the list provided in FIG. 16, that particular table or reference material will be downloaded as shown in FIG. 17. The example shown in FIG. 17 is the Drug Fee Schedule, which is a listing of what Medicare will reimburse for certain drugs.

Figures 18, 19:
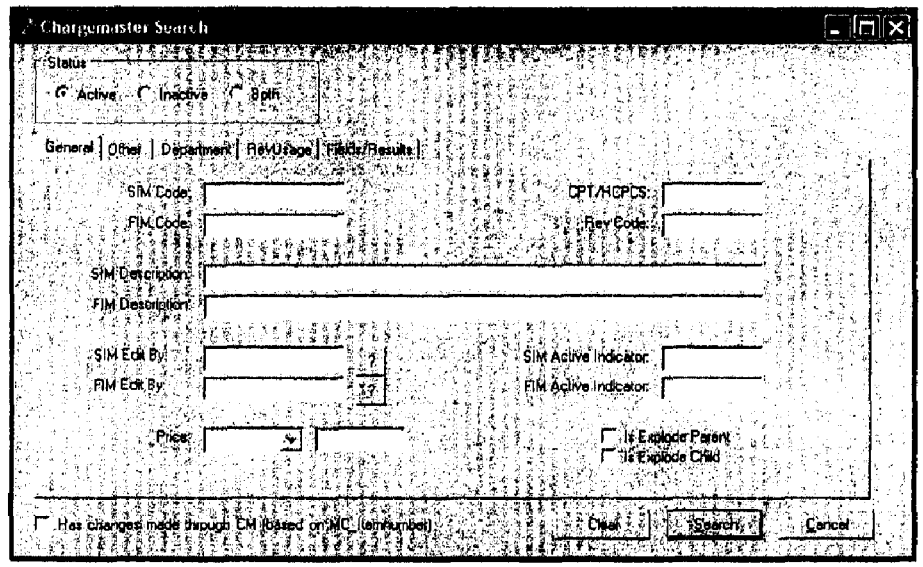

The software, and preferably the portal, has a search feature that allows a user to search the duplicate database. As shown in FIG. 18, search criteria include as examples item description, CPT Code, and/or price. An example of a returned search is shown in FIG. 19. The results are displayed as a sortable grid.

Figure 20:
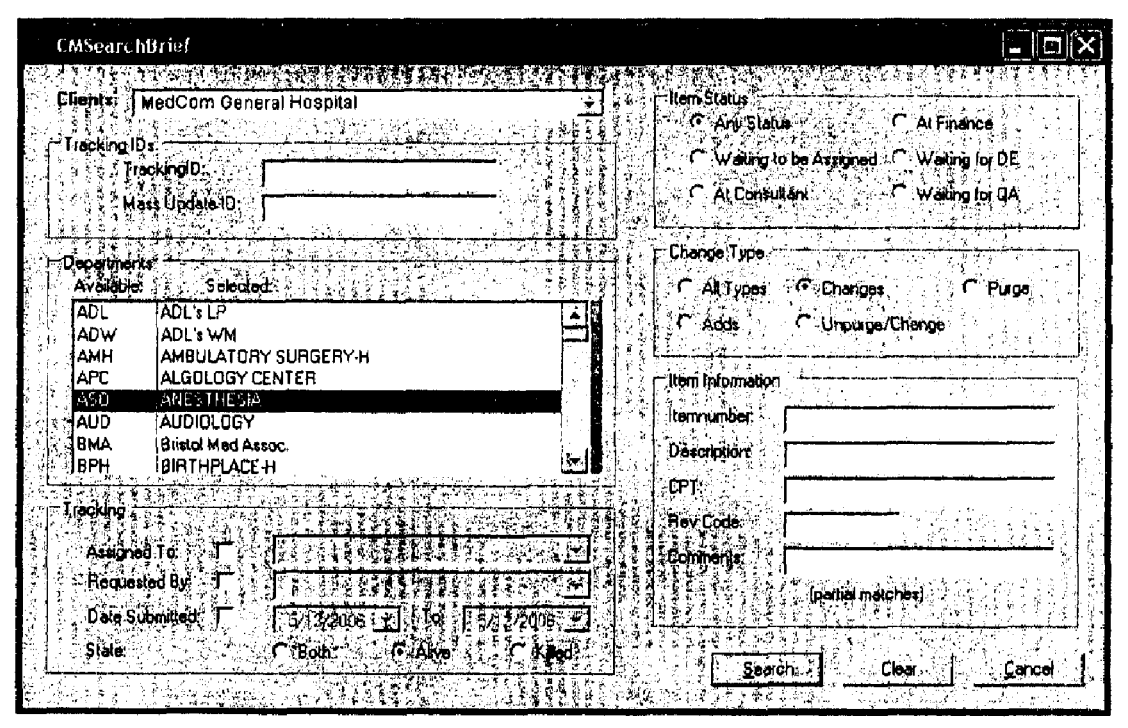

The software also includes an item search that allows a user or a consultant to search a stored list of requested updates for a specific chargeable item. An example of the search screen is shown in FIG. 20. The search can be performed by searching on various criteria, including the identification number, status, type of change, tracking information, and other fields. Once entered, the matching requests are displayed in a sortable grid, an example of which is shown in FIG. 21.

Figure 22:
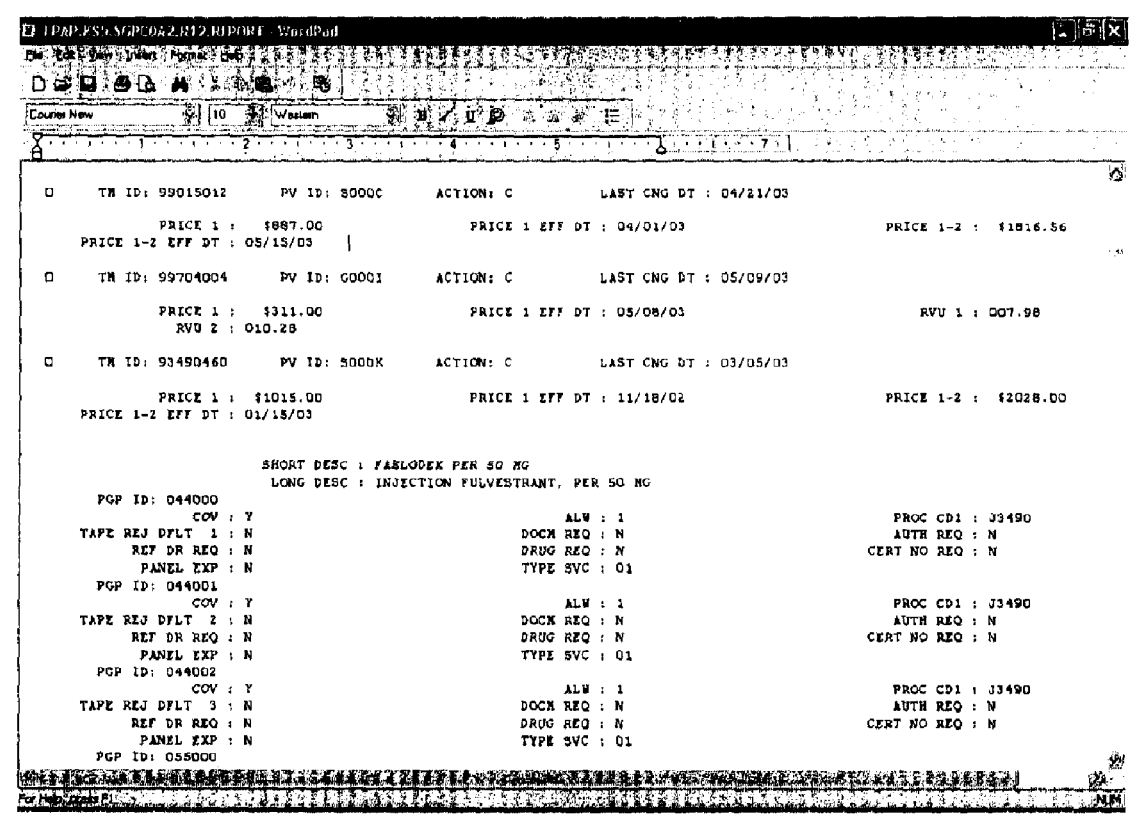

After the approved update is implemented in the primary database, or the item master in this example, a changes report such as the one shown in FIG. 22 is sent to the consulting service by the business. The changes report is preferably sent daily to identify and list all changes or updates to the primary database on a daily basis. The daily changes report can be used as part of the Quality assurance or validation steps. The daily changes report is compared to the Data Entry report shown in FIG. 14 to make sure that the implemented update matches the approved update.

While the foregoing has been set forth in considerable detail, it is to be understood that the drawings, detailed embodiments, and examples are presented for elucidation and not limitation. Design variations, especially in matters of shape, size, and arrangements of parts, may be made but are within the principles of the invention. Those skilled in the art will realize that such changes or modifications of the invention or combinations of elements, variations, equivalents, or improvements therein are still within the scope of the invention as defined in the appended claims.

We claim:

1. A computer-readable storage medium having stored therein a primary database storing a plurality of data entries and a duplicate database having stored therein a temporary working copy of said data entries and instructions including a plurality of approved regulatory changes to said data entries, wherein said instructions are executed by a processor to:
    a. create from said primary database said duplicate database having stored therein said temporary working copy;
    b. convert said temporary working copy to a readable format;
    c. receive a request to update at least one of said data entries in said temporary working copy, wherein said temporary working copy is used as a reference against which to review said update request prior to implementing said update in said primary database;
    d. convert said request to readable format;
    e. review said request in said temporary working copy for compliance with at least one of an entity standard and maintenance or implementation of consistency between at least two users;
    f. approve said request in said temporary working copy when said review determines said request to be compliant with said approved regulatory changes;
    g. in response to said approval in said temporary working copy, update said temporary working copy to update said data entry in said working copy; and
    h. following said approved update to said temporary working copy, replicating said updated temporary working copy to said primary database to update said primary database to create said requested and approved update in said primary database.

2. The computer-readable storage medium as in claim 1, wherein said instructions are executed by said processor to validate said request.

3. The computer-readable storage medium as in claim 1 wherein said instructions are executed by said processor to:
    a. revise said request when said request is reviewed and determined not to be compliant with said plurality of approved regulatory changes; or
    b. identify said request when said request is reviewed and determined not to be complaint with said plurality of approved regulatory changes.

4. The computer-readable storage medium as in claim 1, wherein each said data entry is a line item for one of a plurality of chargeable items.

5. The computer-readable storage medium as in claim 4, wherein said chargeable items comprise at least one of technical chargeable items or professional chargeable items.

6. The computer-readable storage medium as in claim 1, wherein said request is one of the following:
    a. an addition of at least one of said data entries;
    b. a change to at least one of said data entries;
    c. a removal of at least one of said data entries;
    d. reactivation; or
    e. inactivation.

7. The computer-readable storage medium as in claim 1, wherein said primary database is at least one of a hospital item master or a physician item master.

8. The computer-readable storage medium as claimed in claim 1, wherein said plurality of approved regulatory changes includes at least one operator interface.

9. A system for updating a primary database, said primary database storing a plurality of data entries in a first storage medium, said system comprising:
  a. a second storage medium for storing at least one set of instructions that include a plurality of approved regulatory changes to said data entries and a duplicate database having stored therein a temporary working copy of said data entries; and
  b. a processor configured to implement said at least one set of instructions to:
    i. create from said primary database said duplicate database having stored therein said temporary working copy;
    ii. convert said temporary working copy to a readable format;
    iii. receive a request to update at least one of said data entries in said temporary working copy, wherein said temporary working copy is used as a reference against which to review said update request prior to implementing said update in said primary database;
    iv. convert said request to readable format;
    v. review said request in said temporary working copy for compliance with at least one of an entity standard and maintenance or implementation of consistency between at least two users;
    vi. approve said request in said temporary working copy when said review determines said request to be compliant with said approved regulatory changes;
    vii. in response to said approval in said temporary working copy, update said temporary working copy to update said data entry in said working copy; and
    viii. following said approved update to said temporary working copy, replicate said updated temporary working copy to said primary database to update said primary database to create said requested and approved update in said primary database.

10. The system as set forth in claim 9, wherein said processor is further configured to implement said at least one set of instructions to validate said request.

11. The system as set forth in claim 9, wherein said at least one set of instructions are executed by said processor to:
  a. revise said request when said request is reviewed and determined not to be compliant with said plurality of approved regulatory changes; or
  b. identify said request when said request is reviewed and determined not to be complaint with said plurality of approved regulatory changes.

12. The system as set forth in claim 9, further comprising an input device for submitting said request.

13. The system as set forth in claim 9, further comprising a portal, said portal comprising at least one of the following:
  a. an input device;
  b. a status monitor;
  c. at least one reference tool; or
  d. at least one link to a website.

14. The system as set forth in claim 13, wherein said portal is at least one of encoded in software or is a web-based application.

15. The system as set forth in claim 9, wherein each said data entry is a line item for one of a plurality of chargeable items.

16. The system as set forth in claim 15, wherein said chargeable items comprise at least one of technical chargeable items or professional chargeable items.

17. The system as set forth in claim 9 wherein said request is at least one of the following:
  a. an addition of at least one of said data entries;
  b. a change to at least one of said data entries;
  c. a removal of at least one of said data entries;
  d. inactivation; or
  e. reactivation.

18. The system as set forth in claim 9, wherein said primary database is at least one of a hospital item master or a physician item master.

19. The system as claimed in claim 10, wherein said at least one set of instructions to validate comprises instructions to confirm that the update that has been replicated to the primary database is identical to the temporary working copy.

20. The system as claimed in claim 9, wherein said processor is further configured to implement said at least one set of instructions to generate a report, said report summarizing an approved update to said at least one of said data entries in said primary database.

21. The system as in claim 9, wherein said plurality of approved regulatory changes includes at least one operator interface.

22. A computer assisted method for updating a primary database that stores a plurality of data entries, said method comprising the steps of:
  a. creating from said primary database a duplicate database having stored therein a temporary working copy of said data entries;
  b. converting said temporary working copy to a readable format;
  c. receiving a request to update at least one of said data entries in said temporary working copy, wherein said temporary working copy is used as a reference against which to review said update request prior to implementing said update in said primary database;
  d. converting said request to readable format;
  e. reviewing said request in said temporary working copy for compliance with at least one of an entity standard and maintenance or implementation of consistency between at least two users;
  f. approving said request in said temporary working copy when said review determines said request to be compliant with a plurality of approved regulatory changes;
  g. in response to said approval in said temporary working copy, updating said temporary working copy to update said data entry in said working copy; and
  h. following said approval in said temporary working copy, replicating said updated temporary working copy to said primary database to update said primary database to create said requested and approved update in said primary database.

23. The method as in claim 22, further comprising the step of monitoring a status of said request.

24. The method as in claim 22, further comprising the step of:
  a. revising said request when said request is reviewed and determined not to be with said plurality of approved regulatory changes; or
  d. identifying said request when said request is reviewed and determined not to be compliant with said plurality of approved regulatory changes.

25. The method as claimed in claim 22, further comprising the step of validating said request to update.

26. The method as claimed in claim 25, wherein said step of validating comprises the step of confirming that the update that has been replicated to the primary database is identical to the temporary working copy.

27. The method as claimed in claim 22, further comprising the step of generating a report, said report summarizing an approved update to said at least one of said data entries in said primary database.

28. The method as claimed in claim 22, wherein each said data entry is a line item for one of a plurality of chargeable items.

29. The method as claimed in claim 28, wherein said chargeable items comprise at least one of technical chargeable items or professional chargeable items.

30. The method as claimed in claim 22, wherein said request is at least one of the following:
   a. an addition of at least one of said data entries;
   b. a change to at least one of said data entries;
   c. a removal of at least one of said data entries;
   d. inactivation; or
   e. reactivation.

31. The method as claimed in claim 22, wherein said primary database is selected from the group consisting of a hospital item master and a physician item master.

32. The method as claimed in claim 22, wherein said plurality of approved regulatory changes includes at least one operator interface.

33. An apparatus for updating a primary database, said primary database storing a plurality of data entries in a first storage medium, said apparatus comprising:
   a. a second storage medium for storing at least one set of instructions that include a plurality of approved regulatory changes to said data entries;
   b. a duplicate database having stored therein a temporary working copy of said data entries;
   c. means for creating from said primary database said duplicate database having stored therein said temporary working copy;
   d. means for converting said temporary working copy to a readable format;
   e. means for receiving a request to update at least one of said data entries in said temporary working copy, wherein said temporary working copy is used as a reference against which to review said update request prior to implementing said update in said primary database;
   f. means for converting said request to readable format;
   g. means for reviewing said request in said temporary working copy for compliance with at least one of an entity standard and maintenance or implementation of consistency between at least two users;
   h. means for approving said request in said temporary working copy when said review determines said request to be compliant with said approved regulatory changes;
   i. in response to said approval in said temporary working copy, means for updating said temporary working copy to update said data entry in said temporary working copy; and
   i. following said approved update to said temporary working copy, means for replicating said updated temporary working copy to said primary database to update said primary database to create said requested and approved update in said primary database.

34. The apparatus as claimed in claim 33, further comprising:
   a. means for revising said request when said request is reviewed and determined not to be complaint with said plurality of approved regulatory changes; or
   b. means for identifying said request when said request is reviewed and determined not to be complaint with said plurality of approved regulatory changes.

35. The apparatus as claimed in claim 33, further comprising means for validating said request, wherein the means for validating comprises means for confirming that the update that has been replicated to the primary database is identical to the temporary working copy.

36. The apparatus as claimed in claim 33, further comprising means for generating a report, said report summarizing an approved update to said at least one of said data entries in said primary database.

37. The apparatus as claimed in claim 33, wherein each said data entry is a line item for one of a plurality of chargeable items.

38. The apparatus as claimed in claim 37, wherein said chargeable items are selected from the group consisting of technical chargeable items and professional chargeable items.

39. The apparatus as claimed in claim 33, wherein said request is at least one of the following:
   a. an addition of at least one of said data entries;
   b. a change to at least one of said data entries;
   c. a removal of at least one of said data entries;
   d. inactivation; or
   e. reactivation.

40. The apparatus as claimed in claim 33, wherein said plurality of approved regulatory changes includes at least one operator interface.

* * * * *